(12) United States Patent
Jiang et al.

(10) Patent No.: US 11,908,128 B2
(45) Date of Patent: Feb. 20, 2024

(54) SYSTEMS AND METHODS TO PROCESS IMAGES FOR SKIN ANALYSIS AND TO VISUALIZE SKIN ANALYSIS

(71) Applicant: L'Oreal, Paris (FR)

(72) Inventors: Ruowei Jiang, Toronto (CA); Irina Kezele, Toronto (CA); Zhi Yu, Toronto (CA); Sophie Seite, Paris (FR); Frederic Antoinin Raymond Serge Flament, Paris (FR); Parham Aarabi, Richmond Hill (CA); Mathieu Perrot, Orsay (FR); Julien Despois, Paris (FR)

(73) Assignee: L'Oreal, Paris (FR)

( * ) Notice: Subject to any disclaimer, the term of this patent is extended or adjusted under 35 U.S.C. 154(b) by 123 days.

(21) Appl. No.: 16/996,087

(22) Filed: Aug. 18, 2020

(65) Prior Publication Data
US 2021/0012493 A1    Jan. 14, 2021

Related U.S. Application Data

(63) Continuation of application No. PCT/CA2020/050951, filed on Jul. 10, 2020.
(Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0077* (2013.01); *A61B 5/441* (2013.01);
(Continued)

(58) Field of Classification Search
CPC ......... G06T 7/0012; G06T 2207/20076; G06T 2207/20081; G06T 2207/20084;
(Continued)

(56) References Cited

U.S. PATENT DOCUMENTS

| | | | |
|---|---|---|---|
| 6,571,003 B1 * | 5/2003 | Hillebrand | A61B 5/442 382/118 |
| 6,761,697 B2 * | 7/2004 | Rubinstenn | A61B 5/442 600/587 |

(Continued)

FOREIGN PATENT DOCUMENTS

| | | |
|---|---|---|
| JP | 2019-512797 A | 5/2019 |
| JP | 2020-38664 A | 3/2020 |
| KR | 20190051256 A | 5/2019 |

OTHER PUBLICATIONS

Jiang, Luo, Juyong Zhang, and Bailin Deng. "Robust RGB-D Face Recognition Using Attribute-Aware Loss." arXiv preprint arXiv: 1811.09847 (2018). (Year: 2018).*

(Continued)

*Primary Examiner* — Siamak Harandi
(74) *Attorney, Agent, or Firm* — Oblon, McClelland, Maier & Neustadt, L.L.P.

(57) ABSTRACT

Systems and methods process images to determine a skin condition severity analysis and to visualize a skin analysis such as using a deep neural network (e.g. a convolutional neural network) where a problem was formulated as a regression task with integer-only labels. Auxiliary classification tasks (for example, comprising gender and ethnicity predictions) are introduced to improve performance. Scoring and other image processing techniques may be used (e.g. in assoc. with the model) to visualize results such as highlighting the analyzed image. It is demonstrated that the visualization of results, which highlight skin condition affected areas, can also provide perspicuous explanations for the model. A plurality (k) of data augmentations may be made to a source image to yield k augmented images for processing. Activation masks (e.g. heatmaps) produced from processing the k augmented images are used to define a final map to visualize the skin analysis.

22 Claims, 9 Drawing Sheets

Related U.S. Application Data

(60) Provisional application No. 62/878,464, filed on Jul. 25, 2019, provisional application No. 62/872,347, filed on Jul. 10, 2019.

(51) Int. Cl.
*G16H 50/20* (2018.01)
*G06Q 30/0601* (2023.01)

(52) U.S. Cl.
CPC ....... *A61B 5/7267* (2013.01); *G06Q 30/0631* (2013.01); *G06Q 30/0633* (2013.01); *G06Q 30/0641* (2013.01); *G16H 50/20* (2018.01); *G06T 2207/20076* (2013.01); *G06T 2207/20081* (2013.01); *G06T 2207/20084* (2013.01); *G06T 2207/30088* (2013.01); *G06T 2207/30201* (2013.01)

(58) Field of Classification Search
CPC . G06T 2207/30088; G06T 2207/30201; G06T 2200/24; G16H 50/20; G16H 30/40; G16H 50/30; G16H 20/00; G16H 50/70; A61B 5/0077; A61B 5/441; A61B 5/7267; A61B 5/7465; A61B 5/0022; A61B 5/445; A61B 5/6898; G06Q 30/0631; G06Q 30/0633; G06Q 30/0641; G06N 3/048; G06N 3/0464; G06N 3/084; G06N 3/096; G06N 3/045; G06V 10/764; G06V 10/454; G06V 10/82; G06V 40/161; G06V 2201/03; G06F 18/2413
See application file for complete search history.

(56) References Cited

U.S. PATENT DOCUMENTS

| | | | | |
|---|---|---|---|---|
| 6,959,199 | B2 * | 10/2005 | Ohkubo | H04W 52/327 455/503 |
| 7,324,668 | B2 * | 1/2008 | Rubinstenn | G06T 11/00 382/118 |
| 7,437,344 | B2 * | 10/2008 | Peyrelevade | G06Q 30/0601 705/26.7 |
| 7,950,925 | B2 * | 5/2011 | McDaniel | G06Q 30/0601 434/377 |
| 10,311,337 | B1 | 6/2019 | Kim et al. | |
| 2015/0086581 | A1 * | 3/2015 | Li | C12Q 1/689 424/234.1 |
| 2017/0246473 | A1 * | 8/2017 | Marinkovich | G16H 30/40 |
| 2017/0270593 | A1 * | 9/2017 | Sherman | G06Q 30/0251 |
| 2017/0330264 | A1 * | 11/2017 | Youssef | G06F 16/24578 |
| 2018/0289334 | A1 * | 10/2018 | De Brouwer | G16H 50/30 |
| 2018/0350071 | A1 * | 12/2018 | Purwar | G06V 40/171 |
| 2019/0213452 | A1 * | 7/2019 | Ludwinski | G06K 9/6272 |
| 2019/0213453 | A1 * | 7/2019 | Ludwinski | G06K 9/6254 |
| 2019/0220738 | A1 * | 7/2019 | Flank | G06N 3/08 |
| 2019/0237194 | A1 * | 8/2019 | Salvi | A45D 44/00 |
| 2020/0265937 | A1 * | 8/2020 | Anyanwu-Ofili | G16H 10/60 |
| 2020/0388029 | A1 * | 12/2020 | Saltz | G06V 10/267 |
| 2021/0027897 | A1 * | 1/2021 | Rasochova | G16H 10/60 |
| 2022/0021742 | A1 * | 1/2022 | Zhang | G06F 21/32 |

OTHER PUBLICATIONS

Rothe et al., "DEX: Deep Expectation of apparent age from a single image", Looking at People Workshop at International Conference of Computer Vision (ICCV 2015), Dec. 2015 (Year: 2015).*
N. Narang and T. Bourlai, "Gender and ethnicity classification using deep learning in heterogeneous face recognition," 2016 International Conference on Biometrics (ICB), 2016, pp. 1-8, doi: 10.1109/ICB.2016.7550082. (Year: 2016).*
N. Srinivas, H. Atwal, D. C. Rose, G. Mahalingam, K. Ricanek and D. S. Bolme, "Age, Gender, and Fine-Grained Ethnicity Prediction Using Convolutional Neural Networks for the East Asian Face Dataset," 2017 12th IEEE International Conference on Automatic Face & Gesture Recognition (FG 2017), 2017, pp (Year: 2017).*
Selvaraju, Ramprasaath R., et al. "Grad-cam: Visual explanations from deep networks via gradient-based localization." Proceedings of the IEEE international conference on computer vision. 2017. (Year: 2017).*
I. González-Díaz, "DermaKNet: Incorporating the Knowledge of Dermatologists to Convolutional Neural Networks for Skin Lesion Diagnosis," in IEEE Journal of Biomedical and Health Informatics, vol. 23, No. 2, pp. 547-559, Mar. 2019, doi: 10.1109/JBHI.2018.2806962. (Year: 2019).*
Mendes, Danilo Barros, and Nilton Correia da Silva. "Skin lesions classification using convolutional neural networks in clinical images." arXiv preprint arXiv:1812.02316 (2018). (Year: 2018).*
López-Labraca, Javier, et al. "Enriched dermoscopic-structure-based cad system for melanoma diagnosis." Multimedia Tools and Applications 77 (2018): 12171-12202. (Year: 2018).*
International Search Report and Written Opinion dated Sep. 21, 2020 in PCT/CA2020/050951 filed Jul. 9, 2020, 9 pages.
Ruowei Jiang, et al., "A new procedure, free from human assessment that automatically grades some facial skin structural signs. Comparison with assessments by experts, using referential atlases of skin ageing," International Journal of Cosmetic Science, vol. 41, 2019, pp. 67-78.
Ramprasaath R. Selvaraju, et al., "Grad-CAM: Visual Explanations from Deep Networks via Gradient-based Localization," 2017 IEEE International Conference on Computer Vision, 2017, 23 pages.
Luo Jiang et al., "Robust RG-D Face Recognition Using Attribute-Aware Loss", May 17, 2019, pp. 1-15.
Xiaoping Wu et al., "Joint Acne Image Grading and Counting via Label Distribution Learning", Nov. 2, 2019, pp. 10642-10651.
Asami Yonkura et al., "Improving the Generalization of Disease Stage Classification with Deep CNN for Glioma Histopathological Images", IEEE, 2017, pp. 1222-1226.
Hideaki Fujii et al., "Extraction each condition of Acne based on Multispectral Images", IEICE, 2008, pp. 303-306 (with English Abstract).
Jumpei Takagi et al., "Efficient Learning for Distillation of DNN by Self Distillation", IEICE, 2019, pp. 209-214 (with English Abstract).
Kaiming He, Xiangyu Zhang, Shaoqing Ren and Jian Sun. "Deep Residual Learning for Image Recognition." http://image-net.org/challenges/LSVRC/2015/ and http://mscoco.org/dataset/#detections-challenge2015.
Ruowei Jiang et al. "A new procedure, free from human assessment that automatically grades some facial skin structural signs. Comparison with assessments by experts, using referential atlases of skin ageing." International Journal of Cosmetic Science, 2019, 41, 67-78.
Antonella Melina et al. "Artificial Intelligence for the Objective Evaluation of Acne Investigator Global Assessment." Journal of Drugs in Dermatology. vol. 17, Issue 9, pp. 602-605. Sep. 2018.
Hongyu Pan et al. "Mean-Variance Loss for Deep Age Estimation from a Face." pp. 5285-5294, http://www.escience.cn/people/hhan/publication.html and http://chalearnlap.cvc.uab.es.
Rasmus Rothe, Radu Timofte, Luc Van Gool. "DEX: Deep EXpectation of apparent age from a single image." pp. 10-15.
Mark Sandler, Andrew Howard, Menglong Zhu, Andrey Zhmoginov and Liang-Chieh Chen. "MobileNetV2: Inverted Residuals and Linear Bottlenecks." pp. 4510-4520.
Ramprasaath R. Selvaraju et al. "Grad-CAM: Visual Explanations from Deep Networks via Gradient-based Localization." Work done at Virginia Tech. http://gradcam.cloudcv.org. pp. 618-626.
Bolei Zhou, Aditya Khosla, Agata Lapedriza, Aude Oliva and Antonio Torralba. "Learning Deep Features for Discriminative Localization." http://cnnlocalization.csail.mit.edu. pp. 2921-2929.
Fazly Salleh Abas, Benjamin Kaffenberger, Joseph Bikowski, Metin N. Gurcan, "Acne image analysis: lesion localization and classification," Proc. SPIE 9785, Medical Imaging 2016: Computer-Aided Diagnosis, 97850B (Mar. 24, 2016); doi: 10.1117/12.2216444. Event: SPIE Medical Imaging, 2016, San Diego, California, United States.

(56) References Cited

OTHER PUBLICATIONS

A.L. Levshin and M.H. Ritzwoller. "Automated Detection, Extraction, and Measurement of Regional Surface Waves," Pure and Applied Geophysics. Birkhauser Verlag, Basel 2001. pp. 1531-5145.

B Dreno, F Poli, H Pawin, C Beylot, M Faure, M Chivot, N Auffret, D Moyse, F Ballanger. J Revuz. "Development and evaluation of a Global Acne Severity Scale (GEA Scale) suitable for France and Europe." DOI: 10,1111/j.1468-3083.2010.03685.x. Journal of the European Academy of Dermatology and Venereology, 2010. pp. 43-48.

Aamir Saeed Malik et al. "Digital Assessment of Facial Acne Vulgaris." 2014 IEEE.

J. Alfredo Padilla-Medina et al. "Assessment technique for acne treatments based on statistical parameters of skin thermal images." SPIEDigitalLibrary.org/jbo. Journal of BioMedical Optics.

Diederik P. Kingma and Jimmy Lei Ba. "ADAM: a Method for Stochastic Optimization." Published as a conference paper at ICLR 2015. arXiv:1412.6980v9 [cs.LG] Jan. 30, 2017.

Nasim Alamdari et al. "Detection and Classification of Acne Lesions in Acne Patients: A Mobile Application." pp. 0739-0742. 2016.

The Skin Edit. La Roche-Posay Laboratoire Dermatologique. "What is Efficlar Spotscan." Apr. 24, 2019. The Wayback Machine—https://web.archive.org/web/20200814234451/https://www.laroche-posay.co.uk/what . . . Toggle Nav.

European Search Report dated Jun. 16, 2023, issued in European Patent Application No. 20836023.0.

\* cited by examiner

SYSTEMS AND METHODS TO PROCESS IMAGES FOR SKIN ANALYSIS AND TO VISUALIZE SKIN ANALYSIS

CROSS-REFERENCE

This application is a continuation of PCT application PCT/CA2020/050951 filed Jul. 10, 2020. The PCT application claims the domestic benefit of, the following prior US applications: 1) U.S. provisional application No. 62/872,347 filed Jul. 10, 2019 and 2) U.S. provisional application No. 62/878,464 filed Jul. 25, 2019. The entire contents of each prior US application and the PCT application are incorporated herein by reference.

FIELD

This application relates to image processing using neural networks and to dermatology. More particularly this application relates to systems and methods to process images to determine a skin condition severity analysis and to visualize a skin analysis.

BACKGROUND

Accurate skin analysis is an important area in both medical and cosmetics domains. Acne vulgaris is a common dermatological disorder, which affects 85% of the population at some stage during their lives [15]. Efforts have been made to systematically assess the severity of acne by scoring on patients' images. Standard systems, such as Global Acne Severity Scale, have been established to assess each patient or image's acne score by integers based on lesion size, density, type and distribution.

Images such as images of a face present acne vulgaris (a skin condition) in an encoded manner represented by pixels of the images. It is desired to provide a computer implemented method, a computing device, and other aspects that perform or enable performance of automatic image-based diagnostics using deep learning to decode the presence and/or severity of acne vulgaris from the images. It is also desired to process such images to visualize (e.g. through modifying the source image) the skin analysis.

SUMMARY

There are provided systems and methods to process images in relation to skin analysis. In accordance with an embodiment, a learning based model performs dermatological assessment by using a deep neural network (e.g. a convolutional neural network (CNN)). In accordance with an embodiment, a CNN model was trained and evaluated where the problem was formulated as regression task with integer-only labels. In an embodiment, auxiliary classification tasks (for example, comprising gender and ethnicity predictions) are introduced to improve the performance. In an embodiment, other image processing techniques are used in association with the trained deep neural network model to visualize results on the original image. It is demonstrated that the visualization of results, which highlight skin condition (e.g. acne) affected areas, can also provide perspicuous explanations for the model. In an embodiment, a plurality (k) of data augmentations are made to a source image to yield k augmented images for processing. Activation masks (e.g. heatmaps) produced from processing the k augmented images are used to define a final map to visualize the skin analysis.

In accordance with an embodiment, there is provided a skin diagnostic device comprising circuity providing a processing unit coupled to a storage unit to configure the skin diagnostic device to provide: a skin analysis unit to classify pixels of an image using a deep neural network comprising a regressor and a classifier for image classification to generate the skin diagnosis for a skin condition.

In an embodiment, the processing unit and storage unit further configure the skin diagnostic device to provide a visualization unit to annotate the image to visualize the skin diagnosis.

In an embodiment, the processing unit and storage unit further configure the skin diagnostic device to provide a recommendation unit, responsive to the skin diagnosis, to recommend a product for the skin condition.

In an embodiment, the processing unit and storage unit further configure the skin diagnostic device to provide an e-commerce interface with which to purchase products for the skin condition.

In an embodiment, the skin diagnosis comprises an integer value on a scale classifying a severity of the skin condition over the image. In an embodiment, the deep neural network is configured to receive a normalized face image as input and to output a vector which represents a probability distribution over all possible integer values on the scale and applies an activation function to determine the integer value of the skin diagnosis.

In an embodiment, the deep neural network is further configured with auxiliary tasks to determine one or both of an ethnicity prediction and gender prediction.

In an embodiment, the deep neural network comprises an adapted network for image classification which is adapted to generate the skin diagnosis.

In an embodiment, the deep neural network comprises a convolutional neural network (CNN) for image processing. In an embodiment, the CNN comprises a residual network as an encoder having a global pooling operation before final fully connected layers configured to generate regressor and classifier outputs.

In an embodiment, the deep neural network is trained with a combined loss function combining a regressor loss function and a classifier loss function. In an embodiment, the combined loss function conforms to an equation:

$$L=\lambda_{mse}\mathcal{L}_{mse}+\lambda_{ce}\mathcal{L}_{ce}+\lambda_{gender}\mathcal{L}_{gender}+\lambda_{ethnicity}\mathcal{L}_{ethnicity} \quad (2)$$

where:

$\mathcal{L}_{mse}$, $\mathcal{L}_{ce}$, $\mathcal{L}_{gender}$ and $\mathcal{L}_{ethnicity}$ are respective mean square error (MSE), cross-entropy error (CE), gender prediction and ethnicity prediction functions; and $\lambda_{mse}$, $\lambda_{ce}$, $\lambda_{gender}$, and $\lambda_{ethnicity}$ are weighting factors.

In an embodiment, the deep neural network is trained using a dataset of facial image data comprising selfie images from user mobile devices.

In an embodiment, the deep neural network is configured to generate a heatmap to visualize skin diagnosis in association with the image. In an embodiment, the deep neural network is configured to apply a Class Activation Mapping (CAM) technique to generate the heatmap.

In an embodiment, the image comprises a selfie image from a user mobile device.

In an embodiment, the diagnostic device comprises one of a computing device for personal use and a server providing skin diagnostic services via a communications network. In an embodiment, the computing device for personal use comprises one of a smartphone, tablet, laptop, personal computer, or other computing device having or coupled to a camera.

In an embodiment, the recommendation unit provides a treatment product selector responsive to the skin diagnosis to obtain at least one of a product recommendation and a treatment plan recommendation.

In an embodiment, the processing unit and storage unit configure the skin diagnostic device to provide an image acquisition function to receive the image.

In an embodiment, the skin condition is acne vulgaris.

In an embodiment, there is provided a computer implemented method of skin diagnosis comprising: receiving an image and processing the image using a deep neural network configured to classify image pixels to determine skin diagnosis for a skin condition, wherein the deep neural is configured as a regressor and a classifier to determine the skin diagnosis; and visualizing the skin diagnosis in association with the image.

In an embodiment, there is provided a computer implemented method comprising: receiving an image of skin; processing the image with a deep neural network configured to produce a skin analysis result and an activation mask to visualize the skin analysis result in association with the image; and providing the activation mask and image for display. In an embodiment, processing the image comprises, performing a plurality (k) of data augmentations to the image to produce k augmented images for processing by the deep neural network; and processing the k augmented images by the deep neural network to produce k activations masks and defining a final activation mask therefrom. In an embodiment, the k activation masks and final activation mask comprise heatmaps. In an embodiment, the deep neural network produces the respective k activation masks using Grad-CAM technique. In an embodiment, the final activation mask is defined from the k activation masks using averaging. In an embodiment, a threshold is applied to the eliminate values from the k activation masks as averaged. In an embodiment, $2<=k<=20$. In an embodiment, the method comprises normalizing the image of the skin before performing the k data augmentations. In an embodiment, the k data augmentations each comprise one augmentation randomly selected from affine transformations and a horizontal flip operation. In an embodiment, the method comprises providing a product recommendation responsive to the skin analysis result. In an embodiment, the method comprises providing an e-commerce interface with which to purchase one or more products, the interface responsive to the product recommendation. In an embodiment, the product recommendation is associated with a treatment plan for using a recommended product. In an embodiment, the deep neural network is configured to analyze the image for a skin condition. In an embodiment, the skin condition is acne vulgaris. In an embodiment, the deep neural network comprises a convolutional neural network (CNN). In an embodiment, there is provided a computing device comprising circuity which configures the computing device to perform the foregoing method in any of the embodiments.

In an embodiment, there is provide a method comprising: training a convolutional neural network (CNN) configured to classify pixels of an image to determine an skin diagnosis, wherein: the CNN comprises a deep neural network for image classification configured to generate the skin diagnosis; the CNN is configured as a regressor and a classifier to determine the skin diagnosis; and the CNN is trained using a dataset of facial image data comprising selfie images from user mobile devices.

These and other aspects will be apparent to a person of ordinary skill in the art. For any computing device related aspect there is provided a corresponding method aspect and a corresponding computer program product aspect where a (non-transitory) storage device stores instructions, which, when execute by a processing unit of a computing device, configures the computing device to perform a method aspect.

Figure 1:
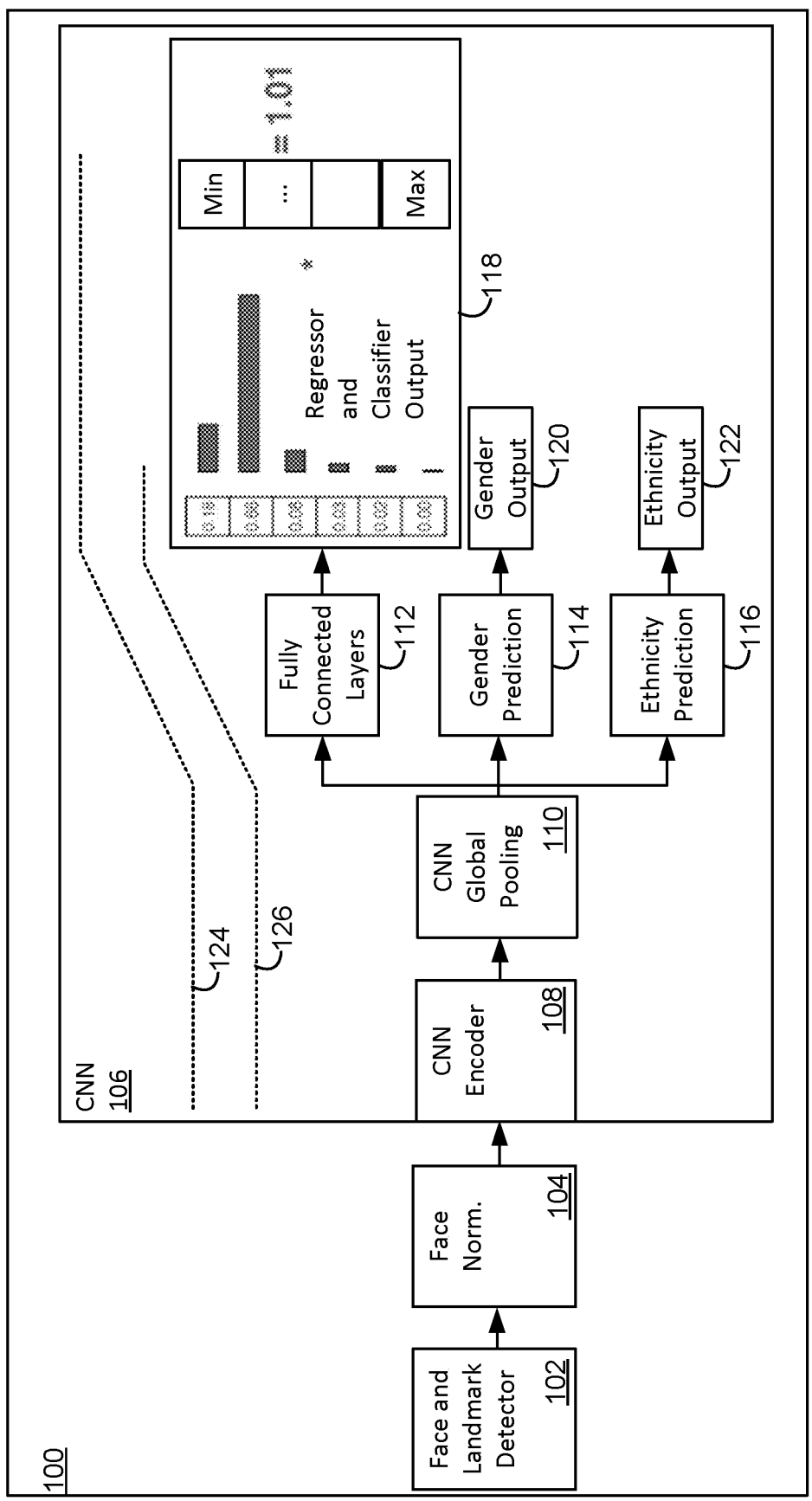
FIG. 1 is a schematic diagram of a storage device of a computing device comprising components of a CNN and output in accordance with an example herein.

In the face examples shown in the drawings, eye regions are masked with black rectangles for purposes of illustration only herein.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

DETAILED DESCRIPTION

Acne vulgaris is a common skin disorder (skin condition) that 85% of the population, especially teenagers, have experienced acne from time to time. To assess severity of acne, individuals need to visit dermatologists and clinicians and rely on their expertise in this domain. A doctor has to manually exam the patient in person and gives an approximate grading based on lesion counts, area affected and other related factors. This method is often time-consuming and labour intensive, which may also results in unreliable and inaccurate result due to reasonable human error. It also requires excessive efforts from the doctor when repeated examination is needed constantly over a period of time.

To minimize human effort needed for this task, many studies have been exploring computer-aided techniques to assess acne severity. Many of the works in this domain, such as [1, 7], require high-standard medical images to be processed by algorithms, which may be difficult to deploy with mobile system. Later works including [8, 2] introduce methods to work with images taken by mobile phones with a number of different steps. However, all these works have been focusing on acne localization and lesion counting [8, 1, 2, 7]. This involves a long pipeline of traditional image processing techniques, such as blob detection and feature extraction, to output masks or region location of lesions. The severity of acne (i.e. acne score) is then computed through formulas based on localization results and the number of lesion detected. One major limitation of this type of method is that the accuracy for acne scoring is grouped with the performance of acne localization and lesion counting. In some cases, lighting condition and skin tone will increase the error rate at various stages of the pipeline and therefore affects the final results significantly.

In a more recent work on acne assessment [9], the authors have achieved remarkable results without lesion counting by using neural networks. They have shown that neural networks can perform very accurately given only image data.

Their method, however, requires a particular type of medical images, which enforces the user to sit in front of a camera device and make 5 specific poses during training and testing. This type of assessment also limits the usage with mobile devices. Another work [16], adapted to images taken by mobile phones, requires multiple iterations of human correction.

In accordance with an example, training techniques of convolutional neural networks (CNN) are expanded. In accordance with an example there is derived a method to fit with a nature of this grading problem: a regression task with integer-only labels. Therefore, in accordance with an example, a system is designed to have one regression objective and another auxiliary classification objective during training. In accordance with an example, added are gender prediction and ethnicity prediction as two extra auxiliary tasks. Experiments on these tasks show improved performance with introducing these tasks. In addition, in accordance with an example, unlike many other works on medical imaging, the model is trained and tested on a selfie dataset consisting of facial images taken by mobile devices and the model demonstrates that this end-to-end model works accurately on selfies in the wild. In accordance with an example, the model is used on mobile devices by uploading only one single image. In accordance with an example, the model outperformed similar work [16] by 3% on acne grading accuracy. Lastly, in accordance with an example, Grad-CAM[13] is used as a visualization tool to show the interpretability of the CNN model.

Dataset

In accordance with an embodiment, an original dataset consists of 5971 images collected from 1051 subjects of five different ethnicities, where three images had been captured by mobile phones for each subject: from the frontal and two profile views. Each subject was assigned an integer score from 0 to 5 using GEA standard [3], by three dermatologists based on their expert assessment on corresponding images. For this scoring model, a dataset of 1877 frontal images are used. Ground truth is defined as the majority score of the scores of the three dermatologists. The dataset is split randomly into train (80%), test (10%) and validation (10%) subsets.

Model Structure

In previous work [5, 11], modern deep learning architectures, such as ResNet [4] and MobileNetV2 [12], have demonstrated excellent ability in learning detailed skin features. Typical approach for this would be transfer learning based on pretrained feature network (e.g. ResNet) by adding a few fully connected layers to classify or regress with respect to proper objective functions. However, as the acne scores are represented by consecutive integers, we introduce an auxiliary classification loss together with regression loss. This idea was inspired by work [11, 10] on age regression task where similar situation applies. In accordance with an embodiment, FIG. 1 is a schematic illustration of a storage device 100 of a computing device providing a deep learning system. The storage device comprises a memory (RAM/ROM), etc. such as for providing instructions to a processing unit, which, in an example, is a graphics processing unit or a processing unit such as of a mobile device or a server.

There is provided a face and landmark detector 102 to receive an image of pixels (not shown) comprising a face for processing. Also provided is a face normalization component 104 to output a normalized face image. Components 102 and 104 pre-process an image to provide a normalized facial image to a CNN 106. CNN 106 comprises encoder component 108 (which, in accordance with the example, comprises a residual network (e.g. ResNet) encoder), a global pooling operations component 110 and decoder or predictor components 112, 114, and 116. Fully connected layers 112 provide respective regressor and classifier output 118. Gender prediction component 114 produces gender output 120 and ethnicity prediction component 116 produces ethnicity output 122. Dotted lines 124 and 126 respectively and schematically show back propagation of loss functions for regressor operations (line 124 represent mean square error regressor loss function) and classifier operations (line 122 representing cross-entropy classifier loss function) to CNN input layer of encode 108 as further described.

Hence, at test time, the CNN model (sometimes referenced as "the model") takes a normalized face image as input and outputs a vector $y = f_\theta(x)$ which represents the probability distribution over all possible integer scores for the acne vulgaris diagnosis scale. The final score is then calculated as softmax expected value (later rounded to output integers):

$$E[f_\theta(x)] = \sum_{i=a}^{b} (f_\theta(x)_i * i) \qquad (1)$$

where a, b are the lower and upper bound for the score range (e.g. the scale).

To construct and train the network, in accordance with the example, the feature extractor was built by adapting an existing trained image processing network. More particularly, a common CNN defined using residual network techniques was adapted. The feature extractor was defined by cropping ResNet50 at its average pooling layer defining CNN encoder 108. A global max pooling layer defining CNN global pooling component 110 was added after the last convolutional block of CNN encoder 108. After features are extracted using these components, the features are further processed using two more fully connected layers (added with Leaky ReLU in between) defining fully connected layers 112. In addition to this, added are two additional branches to help the network to learn better in this cross-race and cross-gender dataset, namely gender prediction block 114 having output 120 and ethnicity prediction block 116 having output 122. Further discussed are experiment results by adding the two branches. It will be understood that, in accordance with an example that is not shown, a base CNN model, (e.g. for image processing), other than ResNet50 is employed. For example, a MobileNet variant, etc. is adapted. In accordance with an example, it is desired to employ a CNN model configured for mobile devices such as to suit to a commercial need. It is understood that the examples herein, including metrics, relate to the adapted ResNet50 'net.

Learning

In accordance with an example, the CNN 106 is trained with four tasks: acne score regression, acne score classification, gender prediction and ethnicity prediction. The CNN 106 (its framework) is trained by optimizing the following objective (defined by a combined loss function):

$$L = \lambda_{mse}\mathcal{L}_{mse} + \lambda_{ce}\mathcal{L}_{ce} + \lambda_{gender}\mathcal{L}_{gender} + \lambda_{ethnicity}\mathcal{L}_{ethnicity} \quad (2)$$

more particularly, $$L = \lambda_{mse}\frac{1}{N_j}\sum_{j=1}^{N}\|E[f_\theta(x_j)] - \hat{y}_j\|^2 + \lambda_{ce}\mathcal{L}_{ce}(Y, f_\theta(X)) + \lambda_{gender}\mathcal{L}_{gender} + \lambda_{ethnicity}\mathcal{L}_{ethnicity} \quad (2)$$

where N is the training batch size and ŷ is the ground truth label.

In accordance with the example, the score classification loss helps the network learn a better probability distribution by minimizing cross-entropy error on the score class probability output. Specifically, this loss encourages the model to output a correct score class before calculating the expected value. As demonstrated in FIG. 1, regression loss is back propagated (shown as line 124) from the final output to an input layer (not specifically shown) of CNN encoder 108 while classification loss is back propagated (shown as line 126) from the probability distribution to the input layer.

In accordance with an example, the gender and ethnicity prediction losses are both calculated by cross-entropy error, which work as the regularization terms in this cross-gender and cross-race dataset. The two losses are also back propagated (not shown) from the prediction layer to the input layer respectively in a similar way to line 126.

Experiments

Implementation Details

Figure 2:
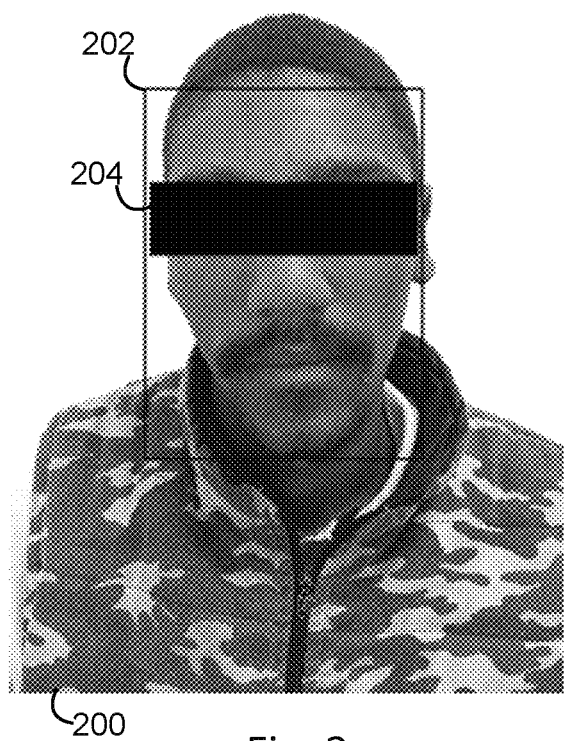
FIG. 2 is an image with a face block.

In accordance with an example, for each image, landmarks are detected such as by using a 60-point face tracker (no-contour points) and a rectangle for the face region is cropped from the input image with some randomness at training time. For each face box (face crop), in the training dataset of unique images randomness is applied to generate further images such as by moving each of leftmost, topmost, rightmost, bottommost point to each corresponding direction, by a random value of [0.08, 0.1]*height, [0.2, 0.3]*width, [0.08, 0.1]*height, [0.07, 0.08]*bottom. Therefore, the face box will be cropped after extension (example shown in FIG. 2 shows an input image and a face box 202. For the purposes of the present disclosure a privacy mask 204 is provided to obscure user identity).

To further augment the source data, in accordance with an example, there is performed random rescaling at scale [0.8, 1.0], random horizontal flip with a probability of 0.5. Each cropped image is resized to 334×448 and the augmented images are centered at [0.485, 0.456, 0.406] with a standard deviation of [0.229, 0.224, 0.225] on RGB channels respectively. In accordance with an example, the CNN is optimized using Adam [6] with learning rate 0:0001. In accordance with an example, a best performance was achieved using the loss function of Eq. 2 where $\lambda_{mse}$=1:0, $\lambda_{ce}$=1:0, $\lambda_{gender}$=0:001, $\lambda_{ethnicity}$=0:001 and ResNet50 as the backbone feature net (i.e. the component defining CNN encoder 108.

Evaluation

As aforementioned, clinically, acne assessment is a regression task with integer-only labels. Therefore, mean absolute error and percentage of testing sample within certain threshold of errors is reported. Errors within 0:5, for example, is also classification accuracy. As a result, in accordance with an example, the model has achieved a mean absolute error of 0:35 with classification error of 71%. In Table 1, shown are results in comparison with prior work on a same dataset of acne assessment. Mean absolute error is reported to give an overview of the regression results and report error percentage within 0:5 and 1:0 to show the level of classification accuracy. As a result, the proposed CNN In accordance with an example, outperforms methods of the prior works on overall classification accuracy. In [16], the experts' performance was also reported to be 67% in terms of experts' agreement to establish a baseline.

TABLE 1

Overall results for using only frontal images and all three photos

| Error | Comparison Model (Spotscan) | Subject Model |
|---|---|---|
| mean absolute error | — | 0.35 |
| error < 0.5 (i.e. classification accuracy) | 68% | 71% |
| error < 1.0 | — | 93% |

Figure 3:
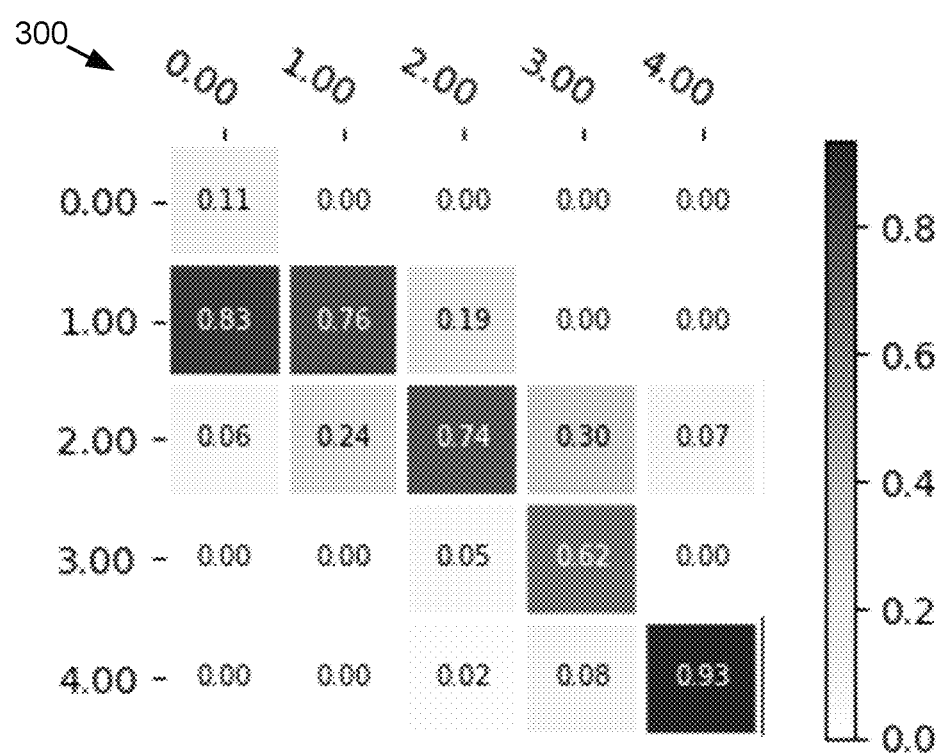
FIG. 3 is a graph showing accuracy of the CNN model, in accordance with an example, by acne vulgaris diagnosis score.

One of the commonly faced challenges is to strike the correct balance among different classes. Overall accuracy often has a strong correlation with performance on the majority class. In acne assessment, using a common scale, an integer score of 1 and a score 2 are typically the majority classes for this kind of problem. Score 0 (no acne), on the other hand, was also hard to distinguish from score 1 (almost no acne) given the size of the data and original score definition. FIG. 3 is a graph 300 showing accuracy by score (e.g. label vs predicted), in accordance with an example. In graph 300, it is shown that the present method achieves a well-balanced accuracy distribution for scores 1 to 4 while class 0 was sometimes misclassified.

Ablation Study

As described, in accordance with an example, a learning method is employed that combines regression with classification learning with a view to improving the accuracy for regression tasks with integer labels in acne assessment. This section includes a discussion and comparison of the following method: 1) using a regression branch with direct output of the score, trained by MSE loss (noted REG); 2) using a classification branch, trained with cross entropy loss (noted CLS); 3) calculate the output based on probability output from classification results, trained with MSE loss (noted REG via CLS); 4) Proposed methods discussed in section 2 (noted REG+CLS).

In Table 2, there is shown a mean absolute error (MAE) and classification accuracy for 4 different training objectives, in accordance with an example. It is seen that treating the skin analysis problem as a pure regression task has achieved a result of 68% on score classification, which is higher than when the problem is formulated as a pure classification task. The proposed training technique, in accordance with an example, out-performed all other training approaches, with smallest MAE and highest classification accuracy. All results in Table 2 are trained with gender and ethnicity branches.

TABLE 2

Results for 4 different methods

| Error | REG | CLS | REG via CLS | REG + CLS |
|---|---|---|---|---|
| mean absolute error | 0.40 | 0.41 | 0.39 | 0.35 |
| error < 0.5 (classification accuracy) | 68% | 66.0% | 66.5% | 71.1% |

Adding Helper Branches

In accordance with an example, in a cross-race and cross-gender dataset, skin features vary for each gender and ethnicity. It is shown that, in accordance with an example, by adding a gender prediction and an ethnicity prediction as auxiliary tasks overall performance is improved. In Table 3, baseline methods refer to training with classification task and regression task but without adding gender and ethnicity prediction branches. The other three columns are results by adding corresponding branches in accordance with examples. Introducing these subsidiary tasks significantly upgraded the model's performance, together by 7.2% increase on classification accuracy and 0.03 decrease for mean absolute error.

TABLE 3

Results when adding helper branches

| Error | baseline | +ethn | +gender | +gender + ethn |
|---|---|---|---|---|
| mean absolute error | 0.38 | 0.37 | 0.36 | 0.35 |
| error < 0.5 (classification accuracy) | 63.9% | 66.5% | 67.0% | 71.1% |

Visualization

Although CNNs have achieved significant progress in numerous vision tasks, such networks do not give direct visual explanation for predictions in many cases. Recent works, such as Class Activation Map (CAM) [14, incorporated herein by reference] and Grad-Gradient-weighted Class Activation Mapping (Grad-CAM) [13, incorporated herein by reference], have proposed ways to visualize such explanation of each prediction result. Interpretability, especially research work targeted for use in industry, is one of the key factors to establish trust between the system and the user.

Figure 4:
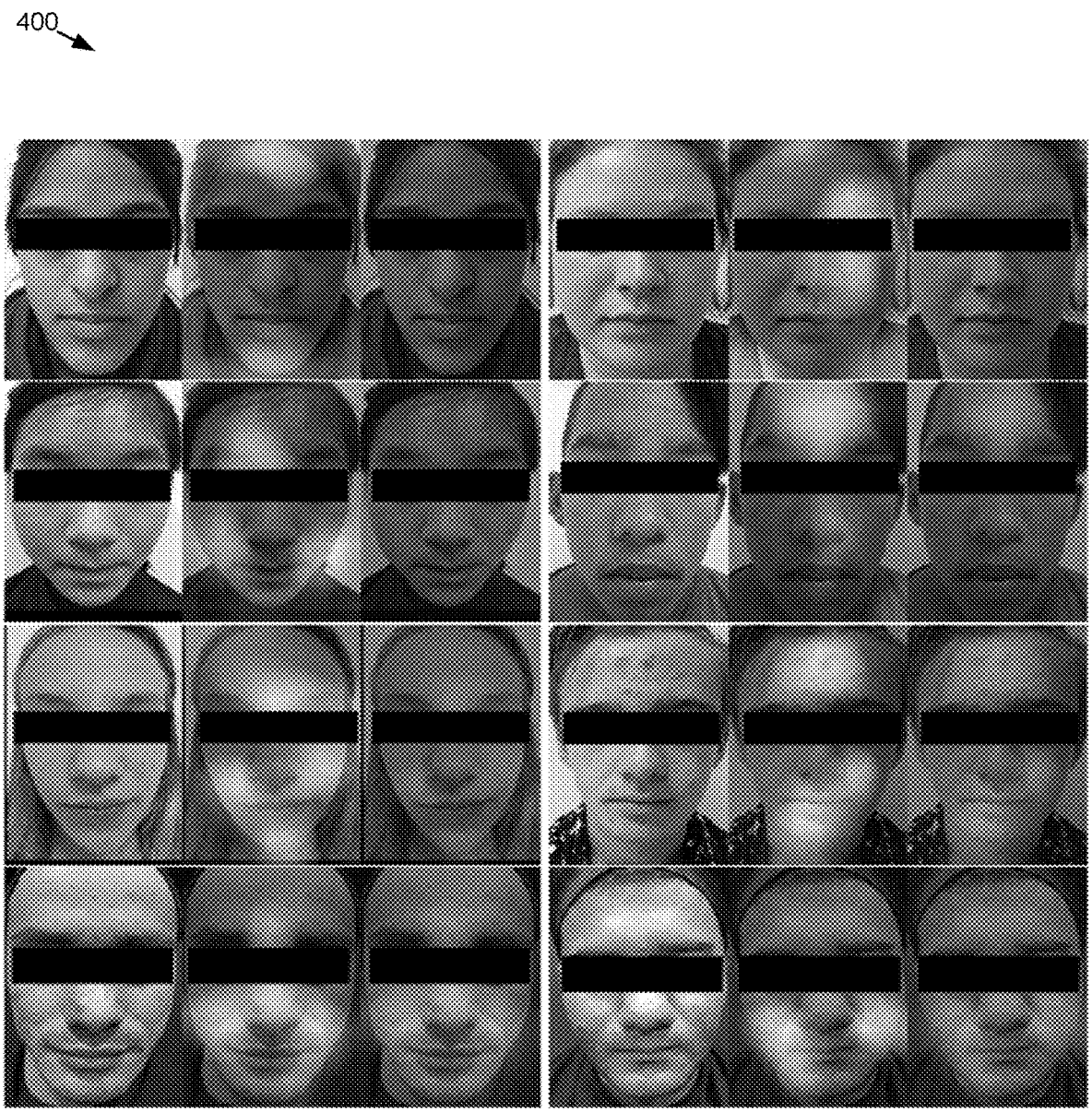
FIG. 4 shows visualization of acne vulgaris diagnosis using heatmaps, in accordance with an example.

FIG. 4 shows results 400 through visualization operations, in accordance with an example, for eight user images in two respective columns and four rows defining respective cells, one cell for each user. Respective input images are modified in response to the acne vulgaris diagnosis. FIG. 4 shows activation maps (heatmaps) generated using Grad-CAM [13] from CNN 106 (the model). FIG. 4 shows different class activation maps from class 1 (mild) in a first or top row to class 4 (severe) in a bottom or fourth row respectively. Further each cell shows an original face image (left image), a first modified face image generated using Grad-CAM (middle image) and a second modified face image generated using Grad-CAM (right image). Each of the first modified face image and the second modified face image comprises the original face image covered (e.g. overlaid) with the respective Grad-CAM generated heatmap, where the first modified face image shows a locally normalized class activation map (CAM) normalized within the image and the second modified face image shows a globally normalized CAM normalized within the dataset. It is understood that pixels of the original image analyzed by the CNN are modified (e.g. RGB channel values are adjusted) using the heatmap to visualize or highlight the areas of the original image responsive to the severity of the acne detected. In an example, the severity is normalized locally within the original image. In an example, the severity is normalized across images in the dataset. For example, visualization is configured to generate heatmap weights based on gradients defined/determined in the last convolutional layer of the trained network. The final heatmap is then normalized within images or dataset. While FIG. 4 shows an array of images for multiple different faces, in an embodiment, visualization presents one or more images of a single (user) face.

Grad-CAM is but one example of a visualization method. In respective embodiments, other visualization methods such as guided back propagation, are also applied to this model.

To adapt to this regression task, in an embodiment, the gradients of class 0 (no acne) with respect to feature map A are negated to obtain counterfactual explanation [13] (shown in Eq. 4). $\alpha_k^0$ is denoted as a heatmap value of the corresponding pixel with respect to class 0, W as width, H as height and $y^0$ as output value of class 0. Based on this equation, lowering the higher values in the activation maps will lead to an increase in class 0 probability with a higher chance.

$$\alpha_k^0 = \frac{1}{W*H}\sum_i^W \sum_j^H -\frac{\partial y^0}{\partial A_{ij}^k} \quad (4)$$

As shown in FIG. 4, acne affected areas have much higher activation values compared to healthy (unaffected) skin. Furthermore, activation values tends to be much higher in severe cases (e.g. class 4) than mild cases (e.g. class 1) when compared globally. In an example, the CNN thus produces an acne vulgaris diagnosis that comprises a score and an area (e.g. of the face) to which the score relates.

Figure 5A:
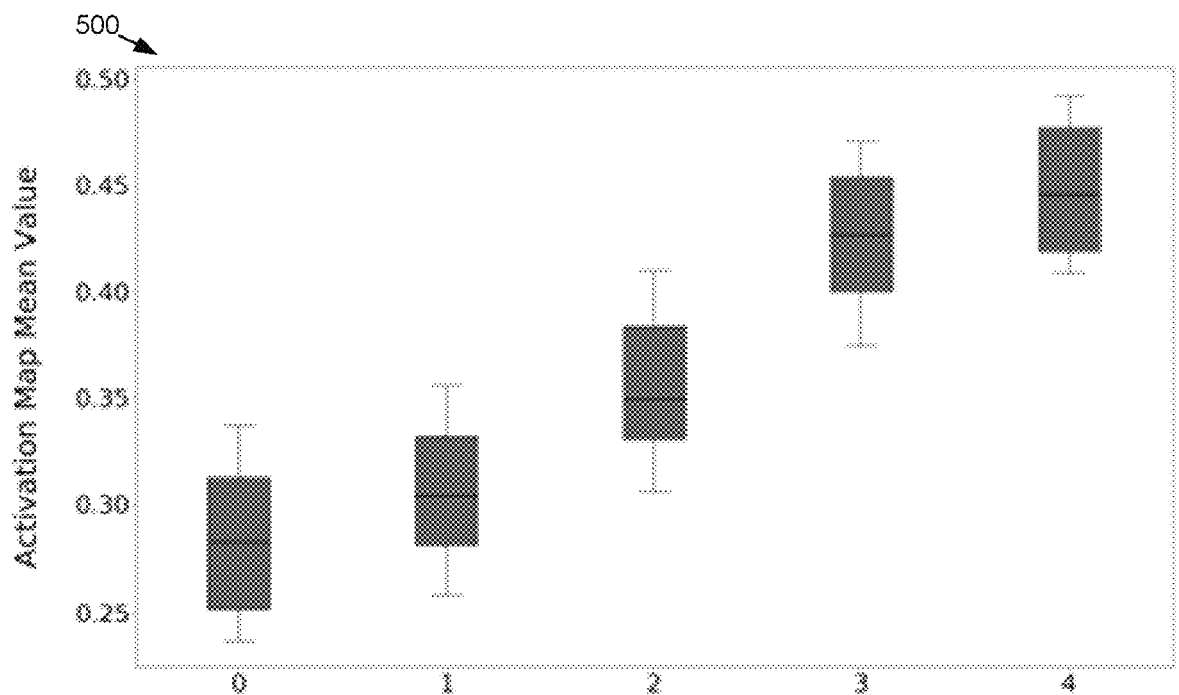
FIGS. 5A and 5B are graphs 500 and 502 showing the relation between activation values of each image versus predicted scores, in accordance with an example.
Figure 5B:
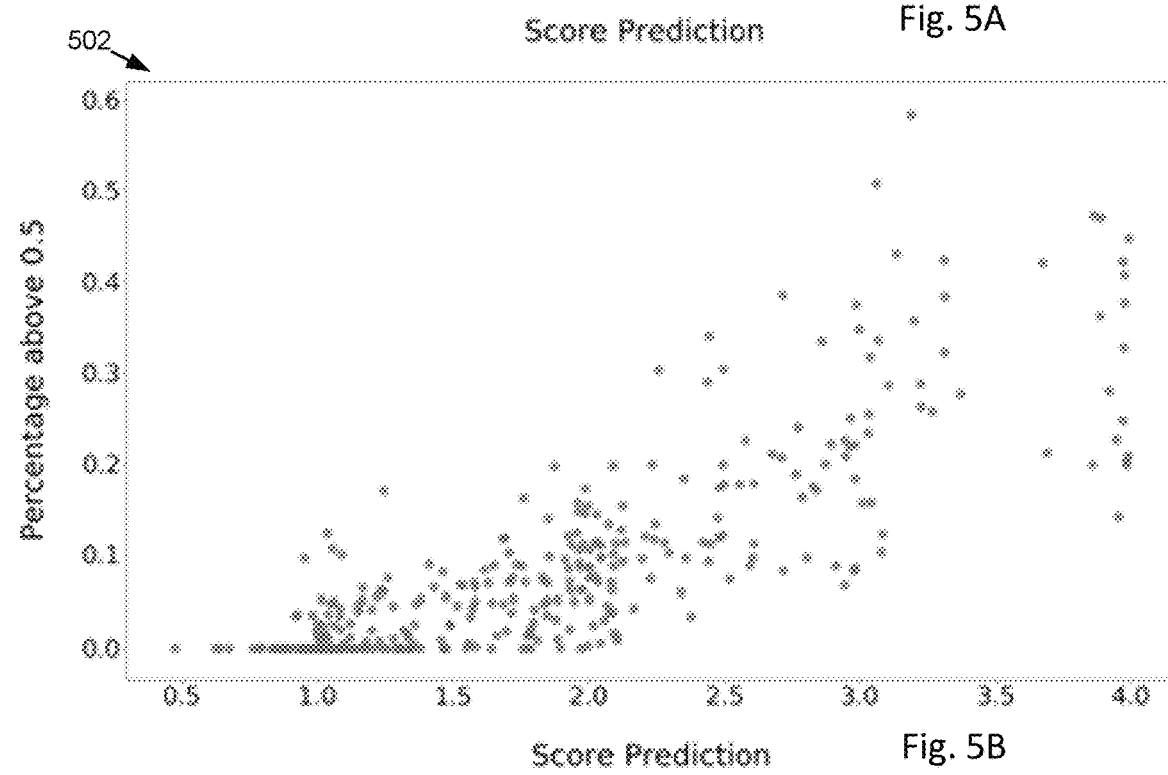

FIGS. 5A and 5B are graphs 500 and 502 showing, in accordance with an embodiment, the relation between activation values of each image versus predicted scores. Interestingly, there is found a positive correlation between "areas affected" and final output. This result images give clear and explainable visualization for the acne assessment model.

In accordance with an example, visualization of results using Grad-CAM are performed using an averaging technique for each respective source image. A method is performed, such as by a computing device, to receive a source image for analysis, perform a plurality k of random data augmentations respectively with the source image to produce k augmented images for analysis, analyze the respective k augmented images using a CNN adapted with the Grad-CAM techniques as described to produce k activation masks/maps and then average the k activations maps to produce a final mask (e.g. by summing and dividing). In an embodiment, the final mask is subject to a threshold. For example, regions where the values are less than a threshold (e.g. 0.4) are removed/eliminated from the heatmap.

In accordance with an example, augmentations comprise affine transformations (such as rotation, scaling, translation) and random horizontal flip. In accordance with an example, augmentations comprise color augmentation. From experimentation, improvements begin for k=2 and stabilize at k=20. In accordance with an example, the source image is analyzed without augmentation as one of the k augmented images (e.g. a null augmentation).

As will be apparent, while the CNN model is also configured to output a score as well as a gender and ethnicity vector for each of the k augmented images that are processed, in accordance with an example, such (score, gender, and ethnicity vector) output is obtained and used from processing one of the k augmented images. The data augmentations and averaging assist to refine the mask, but variations in the score, output (as an example) is not anticipated. Averaging the scores from processing each of the k augmented images (or other class output, for example) is omitted and a single value therefrom is used.

In accordance with an example, mask accuracy is tested by comparing to the mask calculated using ground truth coordinates of acne lesions. For example, a mask is outputted by aggregating all circles centered at the coordinates of acne lesions.

Figure 6:
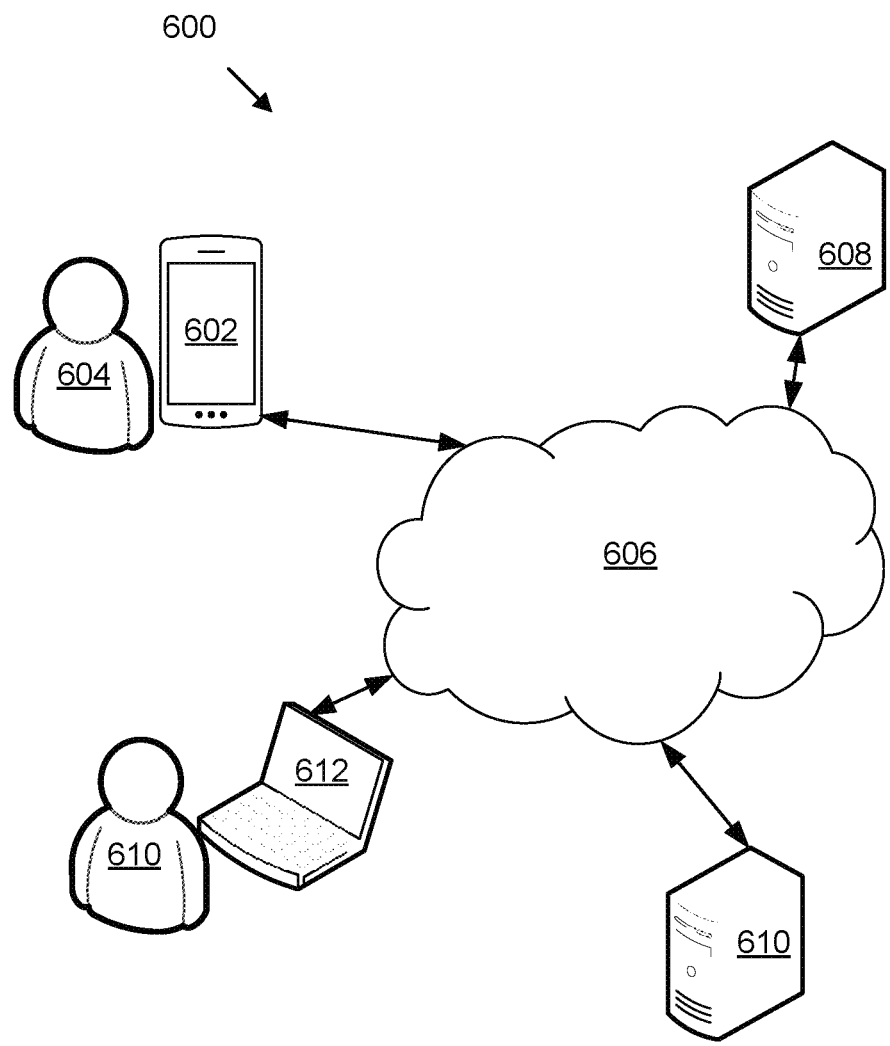
FIG. 6 is an illustration of a computer network providing an environment for various aspects according to embodiments herein.

FIG. 6 is a block diagram of an example computer network 600 in which a computing device 602 for personal use operated by a user 604 is in communication via a communications network 604 with remotely located server computing devices, namely server 606 and server 608. User 604, in accordance with an example, is a consumer and/or a patient of a dermatologist. Also shown is a second user 610 and a second computing device 612 configured for communication via communications network 604. Second user 610, in accordance with an example, is a dermatologist. Computing device 602 is for personal use by a user and is not available to the public. However services from a server are available to the public. Here, the public comprises registered users and/or customers, etc.

Computing device 602, in accordance with an example, is configured to perform skin diagnostics as described herein, namely assessing acne severity such as providing an acne vulgaris diagnosis. In accordance with an example, CNN 106 is stored and utilized on board computing device 602. In accordance with an example, CNN 106 is provided from server 606 such as via a cloud service, web service, etc. from image(s) received from computing device 602.

In accordance with an example, computing device 602 is configured to communicate with server 608 for example to provide acne diagnostic information and receive product/treatment recommendations responsive to a skin diagnosis and/or other information regarding the user e.g. age, gender, etc. In accordance with an example, computing device 602 is configured to communicate skin diagnostic information (which may include image data) to either or both of server 606 and 608, for example, to store in a data store (not shown). In accordance with an example, server 608 (or another service not shown) provides e-commerce services to sell recommended product(s).

Computing device 602 is shown in the example of FIG. 6 as a handheld mobile device (e.g. a smartphone or tablet). However, in accordance with an example, computing device 602 is another form or type of computing device such as a laptop, desktop, workstation, etc. (e.g. having greater processing resources). In accordance with an example, skin diagnosis as described herein is implemented on other computing device types. In accordance with an example, computing device 602 is configured using one or more native applications or browser-based applications, for example.

In accordance with an example, computing device 602 comprises a user device, for example, to acquire one or more images such as a picture of skin, particularly a face, and process the images to provide skin diagnostics. In accordance with an example, skin diagnostics are performed in association with (performing activities of) a skin treatment plan where images are acquired periodically and analyzed to determine skin scores such as for acne as described. The scores are stored (locally, remotely or both) and compared between sessions, for example to show trends, improvement, etc. In accordance with an example, skin scores and/or skin images are accessible to the user 604 of computing device 602. In accordance with an example, the skin scores and/or skin images are made available (e.g. via server 606 or communicated (electronically) in another manner via communication network 604) to another user (e.g. second user 610) of computer system 600 such as a dermatologist. In accordance with an example, second computing device 612 is configured to perform skin diagnostics as described. Second computing device 612 receives images from a remote source (e.g. computing device 602, server 606, server, 608 etc.) and/or captures images via an optical sensor (e.g. a camera) coupled thereto or in any other manner. CNN 106 is stored and used from second computing device 612 or from server 606 as described.

In accordance with an example, an application is provided to perform the skin diagnostics, suggest one or more products and monitor skin changes following one or more applications of the product (which defines one or more treatment sessions in a treatment plan) over a time period. In accordance with an example, the computer application provides workflow such as a series of instructive graphical user interfaces (GUIs) and/or other user interfaces, which are typically interactive and receive user input, to perform any of the following activities:

skin diagnostics such as for acne;
product recommendation such as for a treatment plan;
product purchase or other acquisition;
reminding, instructing and/or recording (e.g. logging) product application for respective treatment sessions;
subsequent (e.g. one or more follow up) skin diagnostics; and
present results (e.g. comparative results);

such as in accordance with a treatment plan schedule to monitor progress of a skin treatment plan. In accordance with an example, any of these activities generate data which is stored remotely for example for user 610 to review, for another individual to review, for aggregation with other user's data to measure treatment plan efficacy, etc.

In accordance with an example, comparative results (e.g. before and after results) are presented via computing device 602 whether during and/or at the completion, etc. of a treatment plan. As noted, in accordance with an example, aspects of skin diagnostics are performed on computing device 600 or by a remotely coupled device (e.g. a server in the cloud or another arrangement).

Figure 7:
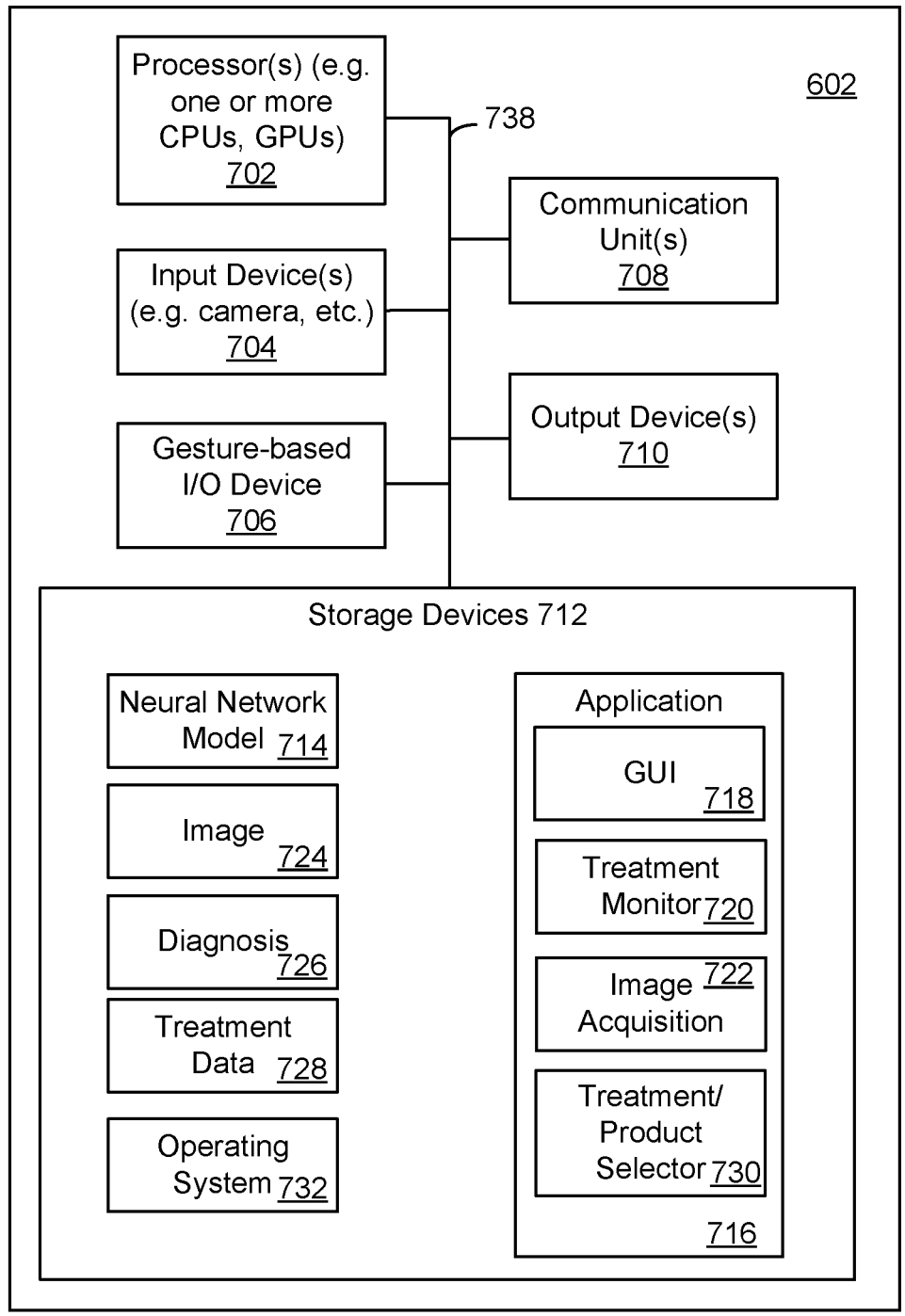
FIG. 7 is a block diagram of a computing device, in accordance with an example, of the computer network of FIG. 6.

FIG. 7 is a block diagram of computing device 602, in accordance with one or more aspects of the present disclosure. Computing device 602 comprises one or more processors 702, one or more input devices 704, a gesture-based I/O device 706, one or more communication units 708 and one or more output devices 710. Computing device 602 also includes one or more storage devices 712 storing one or more modules and/or data. In accordance with an example, modules include deep neural network model 714 (e.g. from CNN 106), application 716 having components for a graphical user interface (GUI 718) and/or workflow for treatment monitoring (e.g. treatment monitor 720), image acquisition 722 (e.g. an interface) and treatment/product selector 730 (e.g. an interface). In accordance with an example, data includes one or more images for processing (e.g. image 724), skin diagnosis data (e.g. respective scores, ethnicity, gender or other user data), treatment data 728 such as logging data related to specific treatments, treatment plans with schedules such as for reminders, etc.)

In accordance with an example, application 716 provides the functionality to acquire one or more images such as a video and process the images to determine skin diagnosis a deep neural network as provided by neural network model 714. In accordance with an example, neural network model 714 is configured as the model shown in FIG. 1 as aforesaid. In another example, neural network model 714 is remotely located and computing device 602, via application 716, communicates the image for processing and return of skin diagnosis data. In accordance with an example, application 716 is configured to perform these previously described activities.

In accordance with an example, storage device(s) 712 store additional modules such as an operating system 732 and other modules (not shown) including communication modules; graphics processing modules (e.g. for a GPU of processors 702); map module; contacts module; calendar module; photos/gallery module; photo (image/media) editor; media player and/or streaming module; social media applications; browser module; etc. Storage devices are sometimes referenced as storage units herein.

In accordance with an example, communication channels 738 couple each of the components 702, 704, 706, 708, 710, 712, and any modules 714, 716 and 732 for inter-component communications, whether communicatively, physically and/or operatively. In some examples, communication channels 738 include a system bus, a network connection, an inter-process communication data structure, or any other method for communicating data.

In accordance with an example, the one or more processors 702 implement functionality and/or execute instructions within computing device 602. For example, processors 702 are configured to receive instructions and/or data from storage devices 712 to execute the functionality of the modules shown in FIG. 5, among others (e.g. operating system, applications, etc.) Computing device 602 stores data/information to storage devices 712. Some of the functionality is described further herein below. In accordance with examples, it is understood that operations do not fall exactly within the modules 714, 716 and 732 of FIG. 5 such that one module assists with the functionality of another.

In accordance with an example, computer program code for carrying out operations are written in any combination of one or more programming languages, e.g., an object oriented programming language such as Java, Smalltalk, C++ or the like, or a conventional procedural programming language, such as the "C" programming language or similar programming languages.

In accordance with an example, computing device 602 generates output for display on a screen of gesture-based I/O device 706 or in some examples, for display by a projector, monitor or other display device. In accordance with an example, it will be understood that gesture-based I/O device 706 is configured using a variety of technologies (e.g. in relation to input capabilities: resistive touchscreen, a surface acoustic wave touchscreen, a capacitive touchscreen, a projective capacitance touchscreen, a pressure-sensitive screen, an acoustic pulse recognition touchscreen, or another presence-sensitive screen technology; and in relation to output capabilities: a liquid crystal display (LCD), light emitting diode (LED) display, organic light-emitting diode (OLED) display, dot matrix display, e-ink, or similar monochrome or color display).

In at least some of the examples described herein, gesture-based I/O device 706 includes a touchscreen device capable of receiving as input tactile interaction or gestures from a user interacting with the touchscreen. In accordance with an example, such gestures include tap gestures, dragging or swiping gestures, flicking gestures, pausing gestures (e.g. where a user touches a same location of the screen for at least a threshold period of time) where the user touches or points to one or more locations of gesture-based I/O device 706. In accordance with an example, gesture-based I/O device 706 also receives non-tap gestures. In accordance with an example, gesture-based I/O device 706 outputs or displays information, such as graphical user interface, to a user. The gesture-based I/O device 706 presents various applications, functions and capabilities of the computing device 602 including, for example, application 716 to acquire images, view images, process the images and display new images, messaging applications, telephone communications, contact and calendar applications, Web browsing applications, game applications, e-book applications and financial, payment and other applications or functions among others.

Although the present disclosure illustrates and discusses a gesture-based I/O device 706 primarily in the form of a display screen device with I/O capabilities (e.g. touchscreen), other examples of gesture-based I/O devices are contemplated to detect movement. In accordance with an example, such do not comprise a screen per se. In such a case, computing device 602 includes a display screen or is coupled to a display apparatus to present new images and GUIs of application 716. In accordance with an example, computing device 602 receives gesture-based input from a track pad/touch pad, one or more cameras, or another presence or gesture sensitive input device, where presence means presence aspects of a user including for example motion of all or part of the user.

In accordance with an example, one or more communication units 708 communicate with external devices (e.g. server 606, server 608, second computing device 612) such as for the purposes as described and/or for other purposes (e.g. printing) such as via communications network 604 by transmitting and/or receiving network signals on the one or more networks. In accordance with an example, the communication units include various antennae and/or network interface cards, chips (e.g. Global Positioning Satellite (GPS)), etc. for wireless and/or wired communications.

In accordance with an example, input devices 704 and output devices 710 include any of one or more buttons, switches, pointing devices, cameras, a keyboard, a microphone, one or more sensors (e.g. biometric, etc.), a speaker, a bell, one or more lights, a haptic (vibrating) device, etc. One or more of same are coupled via a universal serial bus (USB) or other communication channel (e.g. 738). In accordance with an example, a camera (an input device 804) is front-oriented (i.e. on a same side as) to permit a user to capture image(s) using the camera while looking at the gesture based I/O device 706 to take a "selfie".

In accordance with examples, the one or more storage devices 712 take different forms and/or configurations, for example, as short-term memory or long-term memory. In accordance with an example, storage devices 712 are configured for short-term storage of information as volatile memory, which does not retain stored contents when power is removed. Volatile memory examples include random access memory (RAM), dynamic random access memory (DRAM), static random access memory (SRAM), etc. Storage devices 712, in some examples, also include one or more computer-readable storage media, for example, to store larger amounts of information than volatile memory and/or to store such information for long term, retaining information when power is removed. Non-volatile memory examples include magnetic hard discs, optical discs, floppy discs, flash memories, or forms of electrically programmable memory (EPROM) or electrically erasable and programmable (EEPROM) memory.

Though not shown, in accordance with an example, a computing device is configured as a training environment to train neural network model 714 for example using the network as shown in FIG. 4 along with appropriate training and/or testing data.

In accordance with an example, the CNN 106/neural network model 714 is adapted to a light architecture for a computing device that is a mobile device (e.g. a smartphone or tablet) having fewer processing resources than a "larger" device such as a laptop, desktop, workstation, server or other comparable generation computing device.

In accordance with an example, second computing device 612 is similarly configured as computing device 602. Second computing device 612 presents GUIs such as to request and display image(s) and acne diagnoses from data stored at server 606 for different users, etc.

Figure 8A:
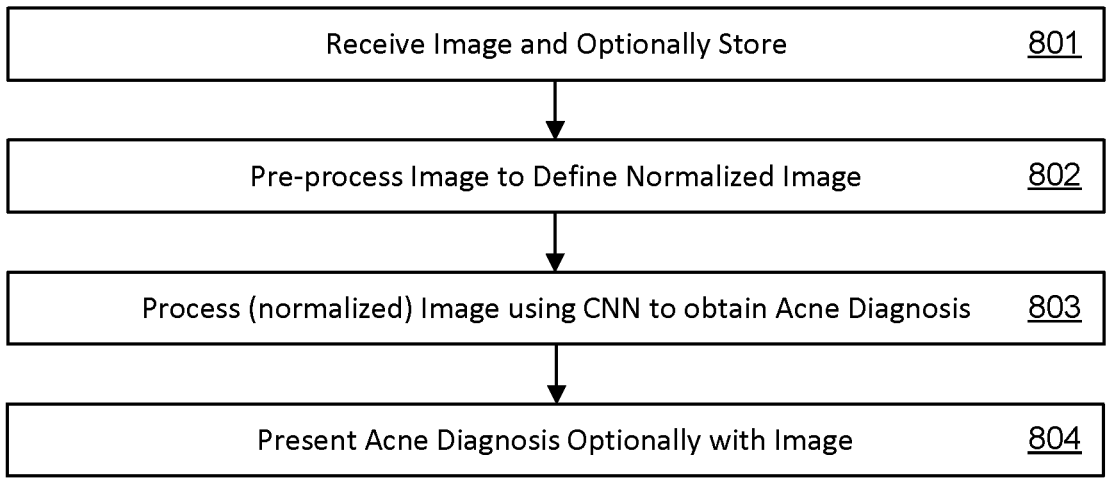
FIGS. 8A-8B and 9 are flowcharts of operations of a computing device according to an embodiment herein.
Figure 8B:
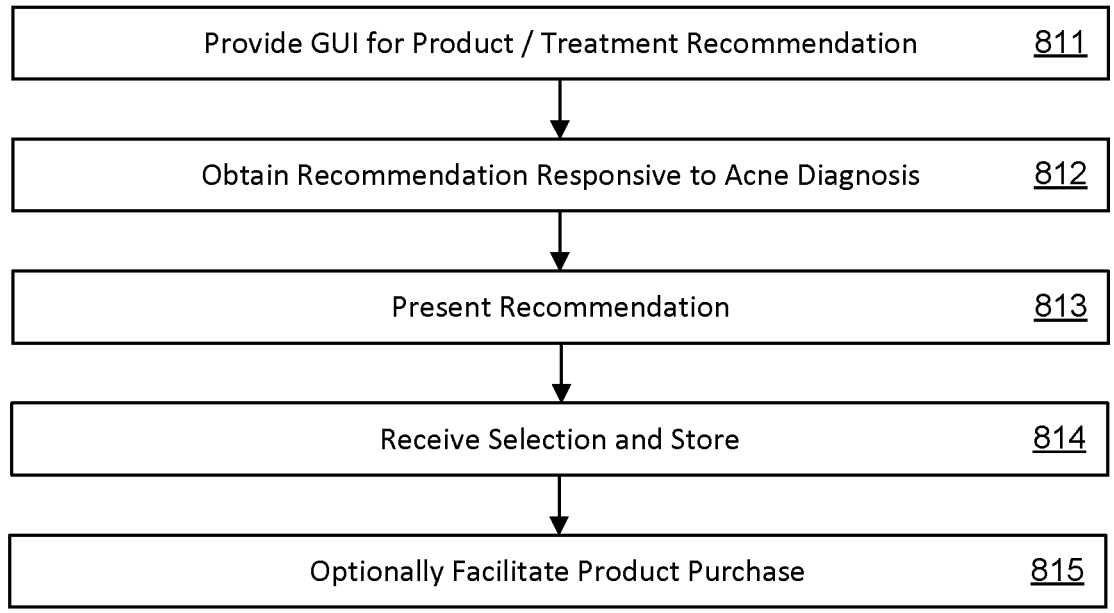

In accordance with an example, FIGS. 8A-8B are flowcharts of operations 800 and 810 respectively such as for computing device 602 (or 610) in accordance with an example. Operations 800 relate to a user of computing device 602 using an application such as application 716 to take a selfie comprising an image of the user's face to perform skin diagnoses for acne severity. At 801, the image is received at the processor such as via a camera or other manner (e.g. from a message attachment).

At 802, the image is pre-processed to define a normalized image to present to the CNN. The image is, variously, centered and cropped to a specific size (resolution) to present like sized images to CNN as per its training. At 803, the normalized image is processed using the CNN 106 (neural network model 714) to generate the acne vulgaris diagnosis (e.g. an integer score). The gender and ethnicity output is also generated. The acne diagnosis, gender and ethnicity vector (or a single value thereof) is presented at 804 such as via a GUI. In accordance with an example, the GUI presents the image and/or normalized image and an adapted image visualizing the acne using a heatmap as described. In accordance with an example, the GUI presents the image and then transitions to presenting the adapted image visualizing the acne, once available.

FIG. 8B shows operations 810. At 811 a GUI is presented (in accordance with an example, a GUI is presented for any of the operations 800, 810) to initiate a product and/or treatment recommendation. Input is received to invoke a performance. At 812 a recommendation is obtained. To obtain the recommendation, in accordance with an example, operations of device 602 comprise communicating acne diagnosis information (e.g. scores, ethnicity vector, gender vector, image, user information, etc.) to a remote server such as server 608 to receive a recommendation. In accordance with an example, the recommendation includes a product or products and a regime of application to an area of skin and in association with a treatment plan having a schedule. At 813 the recommendation is presented such as via the GUI. In accordance with an example, more than one recommendation is received and presented. At 814 a selection is made indicating acceptance of a recommendation. In accordance with an example, the selection is stored (logged) and a treatment monitoring feature or function (not shown) of computing device 602 is initiated, for example. In accordance with an example, at 815, a product purchase is facilitated such as via server 608, or another server.

Though not illustrated, In accordance with an example, monitoring is responsive to treatment plan (e.g. as described in data) received by computing device 602 or accessible to it such as via a browser. In accordance with an example, a treatment plan has a schedule (e.g. morning and evening applications of a product), once a week application of a second product, etc. In accordance with an example, a user is reminded of the schedule such as via notifications, which are native application based or via another means such as a calendar application. In accordance with an example, a GUI is provided to facilitate a treatment activity, for example, to record its occurrence and/or to provide instructions to perform the activity. Input is received such as a confirmation that the activity was performed. In accordance with an example, an image is included to record the activity. In accordance with an example, respective data is logged (locally and/or remotely). In accordance with an example, monitoring measures how closely the treatment plan is followed. In accordance with an example, a product repurchase is facilitated. For example, in accordance with an example, responsive to treatment monitoring, it is determined that product quantity on hand is running out.

Though not illustrated, in accordance with an example, a comparison activity is performed, (e.g. performed as a monitoring activity). A GUI for comparison is provided to instruct a user, etc. A new image (e.g. compared to an initial image received at 601) is received and (optionally) stored. A subsequent acne vulgaris diagnosis is performed using the CNN 106 on the new image (e.g. as normalized etc., similar to operations 600). A GUI presents a comparison of the treatment results, using the initial and subsequent acne diagnoses, optionally with first and new images, optionally with such one or more images modified using heatmaps.

Though not shown, in accordance with an example, data received or generated for the operations 800, 810 and the monitoring and/or comparison activities is communicated for remote storage such as to server 606.

In accordance with an example, acne diagnoses, and subsequent diagnoses (optionally with other monitoring) and providing data for aggregation enables product efficacy and/or fraudulent claims study of products and treatments. In accordance with an example, the data is gathered, analyzed and presented to dermatologists and/or other professionals and/or users. Thus the technologies and/or methodologies of the various examples herein facilitate a distributed study model such as for acne skin treatment.

Figure 9:
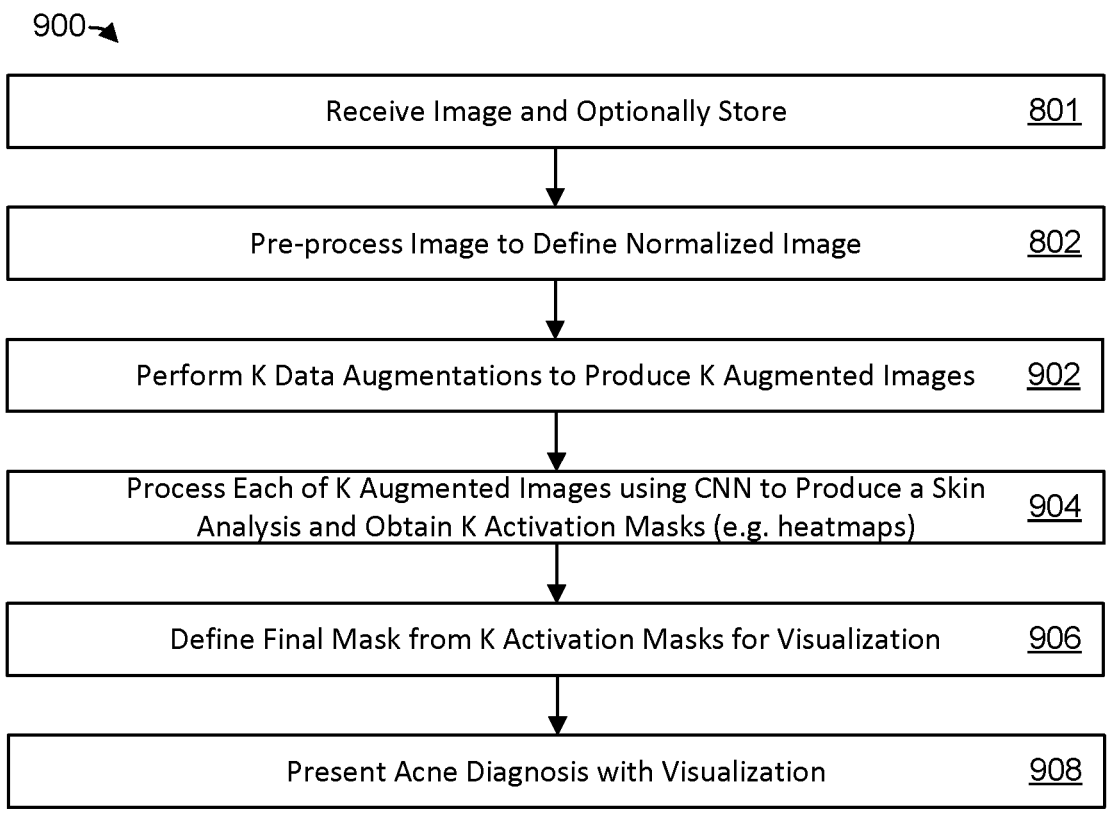

FIG. 9 is a flowchart of operations 900 such as for computing device 602 (or 610) in accordance with an example. Operations 900 are similar to operations 800 and relate to a user of computing device 602 using an application such as application 716 to take a selfie comprising an image of the user's face to perform skin diagnoses for acne severity. In the present operations 900, k data augmentations are performed and k images analyzed to produce a visualization.

As the operations 900 in the example are similar, references from operations 800 are repeated in FIG. 9. At 801, the image is received at the processor such as via a camera or other manner (e.g. from a message attachment).

At 802, the image is pre-processed to define a normalized image to present to the CNN. The image is, variously, centered and cropped to a specific size (resolution) to present like sized images to CNN as per its training. At 902, data augmentation is performed on the normalized image such that k random data augmentations are respectively applied to define k augmented images for analysis. In an example, operations 802 and 902 are reversed in order. The source image is augmented and then normalized though this may repeat certain operations.

At 904 each of the k augmented images is processed using the CNN 106 (neural network model 714) to generate an acne vulgaris diagnoses (e.g. an integer score) and k activation masks (e.g. heatmaps such as described using Grad-CAM). Gender and ethnicity output are also generated. At 906, a final mask is defined from the k activation masks. In the example, the k activation masks are averaged and a threshold applied as described to generate the final mask/heatmap as a visualization of the skin analysis. At 908 the acne diagnosis is presented such as via a GUI with visualization relative to the original image. In the example, the heatmap is overlaid on the original image to visualize the analysis/diagnosis. Optionally gender and ethnicity vector (or a single value thereof) is presented with the visualization.

Figure 10A:
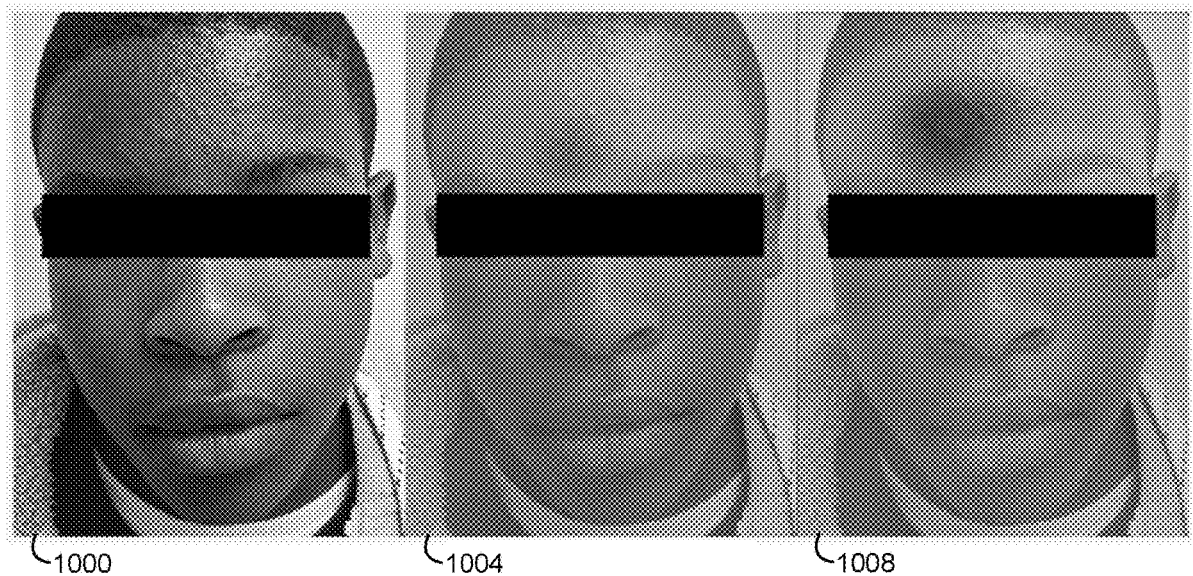
FIGS. 10A and 10B show respective source images and visualizations of the skin analysis, in accordance with an example.
Figure 10B:
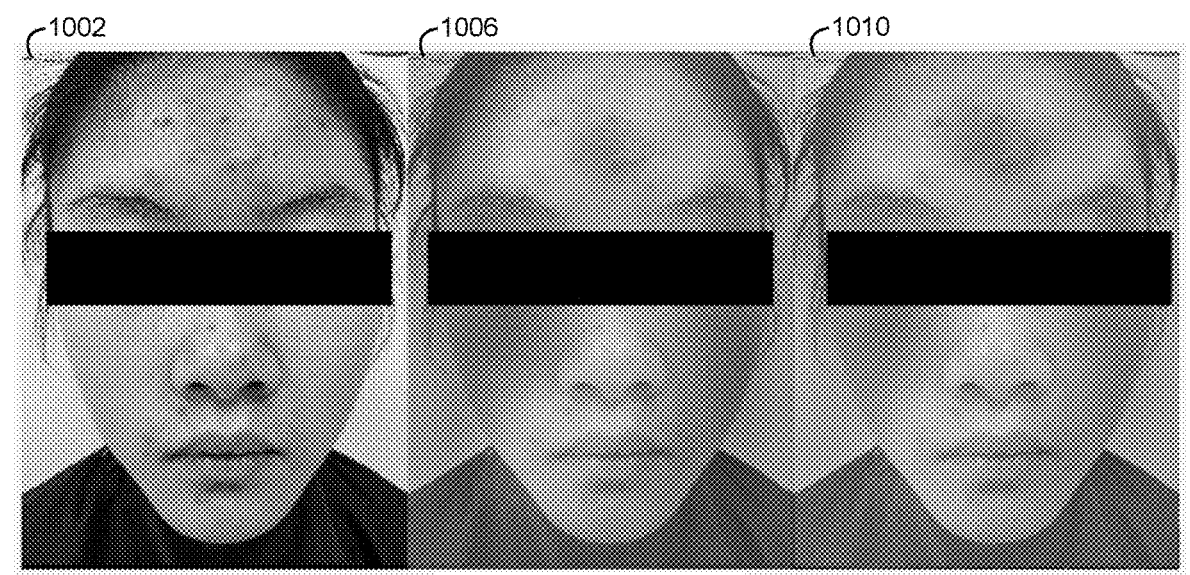

FIGS. 10A and 10B show respective source images 1000, 1002 and visualizations 1004, 1006, 1008 and 1010 of the skin analysis, in accordance with an example. Each of the first modified face images 1004 and 1006 and each of the second modified face images 1008 and 1010 comprises the respective original face image 1000, 1002 covered (e.g. overlaid) with the respective Grad-CAM generated heatmap produced using the averaging technique. The first modified face images 1004 and 1006 show a locally normalized class activation map (CAM) that is normalized within the image and the second modified face images 1008 and 1010 show a globally normalized CAM within all images of the same number of augmentations. With reference to FIG. 10B, the skin condition presents in the original image 1002 most severely in the central forehead region, less severely around the mouth and upper chin and less severely again over the nose. Visualizations 1006 and 1010 blur the skin details of original image 1002 to highlight skin regions using heatmaps. In an embodiment, colour overlays are used. Colours and/or gradients, etc. are aligned with severity results (e.g. skin analysis integer values). The heatmaps of visualizations 1006 and 1010 each highlight the regions where the skin condition presents and minimize other regions of the skin (e.g. cheeks, lower chin) where the skin condition does not present in the original image 1002. For example, the cheek regions are darkened and the regions where the skin condition is present are highlighted relative to the score therefor as normalized using local or global data. FIG. 10A shows similar visualizations for the skin condition which is most sever in the forehead region. Highlighting may be variously granular within a section showing the skin condition. For example, in the forehead region of 1004 and 1008 or 1006 and 1010, the portion of the region where the skin condition is detected is highlighted relative to its severity.

In this disclosure there is described, in one or more examples, a method to train CNNs on acne severity assessment regression task with integer only labels. While previous works often have complicated pipeline and specific requirements for images, the described end-to-end model for acne assessment can work with images captured by mobile devices and can be used via mobile or Web applications in real-time. With well-adapted loss functions and training techniques, 3% better results were achieved compared to similar work.

In addition to computing device aspects, shown in one or more examples, a person of ordinary skill will understand that computer program product aspects are disclosed, where instructions are stored in a non-transient storage device (e.g. a memory, CD-ROM, DVD-ROM, disc, etc.) to configure a computing device to perform any of the method aspects described herein.

It will be understood that a computing device comprises circuiting such as a processing unit coupled to a storage unit. Such circuitry configures the computing to device to provide various features and functions and/or to perform an applicable method. The circuitry may be (at least logically) considered to define respective functional units. An example of a functional unit is a skin analysis unit and/or a visualization unit, etc. having the features as described herein. Others will be apparent. In an embodiment, there is provided a skin analysis unit to classify pixels of an image using a deep neural network comprising a regressor and a classifier for image classification to generate the skin diagnosis for a skin condition.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise" and "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers characteristics, compounds, chemical moieties or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

REFERENCES

1. Abas, F. S., Kaffenberger, B., Bikowski, J., Gurcan, M. N.: Acne image analysis: lesion localization and classification. In: Medical Imaging 2016: Computer-Aided Diagnosis. vol. 9785, p. 97850B. International Society for Optics and Photonics (2016)
2. Alamdari, N., Tavakolian, K., Alhashim, M., Fazel-Rezai, R.: Detection and classification of acne lesions in acne patients: A mobile application. In: 2016 IEEE International Conference on Electro Information Technology (EIT). pp. 0739-0743. IEEE (2016)
3. Drno, B., Poli, F., Pawin, H., Beylot, C., Faure, M., Chivot, M., Auffret, N., Moyse, D., Ballanger, F., Revuz, J.: Development and evaluation of a global acne severity scale (gea scale) suitable for France and Europe: Global acne assessment scale. Journal of the European Academy of Dermatology and Venereology: JEADV 25, 43-8 (April 2010). URL doi.org/10.1111/j.1468-3083.2010.03685.x
4. He, K., Zhang, X., Ren, S., Sun, J.: Deep residual learning for image recognition. In: Proceedings of the IEEE conference on computer vision and pattern recognition. pp. 770-778 (2016)
5. Jiang, R., Kezele, I., Levinshtein, A., Flament, F., Zhang, J., Elmoznino, E., Ma, J., Ma, H., Coquide, J., Arcin, V., Omoyuri, E., Aarabi, P.: A new procedure, free from human assessment, that automatically grades some facial skin structural signs. Comparison with assessments by experts, using referential atlases of skin aging. International Journal of Cosmetic Science 41 (January 2019). URL doi.org/10.1111/ics.12512.
6. Kingma, D. P., Ba, J.: Adam: A method for stochastic optimization. CoRR abs/1412.6980 (2014), URL arxiv.org/abs/1412.6980
7. Malik, A. S., Ramli, R., Hani, A. F. M., Salih, Y., Yap, F. B. B., Nisar, H.: Digital assessment of facial acne vulgaris. In: 2014 IEEE International Instrumentation and Measurement Technology Conference (I2MTC) Proceedings. pp. 546-550. IEEE (2014)
8. Maroni, G., Ermidoro, M., Previdi, F., Bigini, G.: Automated detection, extraction and counting of acne lesions for automatic evaluation and tracking of acne severity. In: 2017 IEEE Symposium Series on Computational Intelligence (SSCI). pp. 1-6. IEEE (2017)
9. Melina, A., Dinh, N. N., Tafuri, B., Schipani, G., Nistic_o, S., Cosentino, C., Amato, F., Thiboutot, D., Cherubini, A.: Arti_cial intelligence for the objective evaluation of acne investigator global assessment. Journal of drugs in dermatology: JDD 17(9), 1006-1009 (2018)
10. Pan, H., Han, H., Shan, S., Chen, X.: Mean-variance loss for deep age estimation from a face. In: Proceedings of the IEEE Conference on Computer Vision and Pattern Recognition. pp. 5285-5294 (2018)
11. Rothe, R., Timofte, R., Van Gool, L.: Dex: Deep expectation of apparent age from a single image. In: Proceedings of the IEEE International Conference on Computer Vision Workshops. pp. 10-15 (2015)
12. Sandler, M., Howard, A., Zhu, M., Zhmoginov, A., Chen, L. C.: Mobilenetv2: Inverted residuals and linear bottlenecks. In: The IEEE Conference on Computer Vision and Pattern Recognition (CVPR) (June 2018)
13. Selvaraju, R. R., Cogswell, M., Das, A., Vedantam, R., Parikh, D., Batra, D.: Grad-cam: Visual explanations from deep networks via gradient-based localization. In: Proceedings of the IEEE International Conference on Computer Vision. pp. 618-626 (2017)
14. Zhou, B., Khosla, A., Lapedriza, A., Oliva, A., Torralba, A.: Learning deep features for discriminative localization. In: Proceedings of the IEEE conference on computer vision and pattern recognition. pp. 2921-2929 (2016)
15. J. P.-O. N. V.-A. A. R.-A. J. D.-C. J. Alfredo Padilla-Medina, Francisco Len-Ordoez, Assessment technique for acne treatments based on statistical parameters of skin thermal images, Journal of Biomedical Optics 19 (4) (2014) 1-8-8. doi:10.1117/1.JBO.19.4.046019. URL doi.org/10.1117/1.JBO.19.4.046019
16. La Roche Posay: What is effaclar spotscan? (2019), URL www.laroche-posay.co.uk/what-is-effaclar-spotscan, last accessed=2019 Jun. 25

What is claimed is:

1. A skin diagnostic device comprising circuitry providing a processing unit coupled to a storage unit to configure the skin diagnostic device to provide:
a skin analysis unit to classify pixels of an image, that is a selfie face image from a user mobile device, using a deep neural network, which is already trained using a dataset of facial image data comprising selfie face images from user mobile devices, comprising a regressor and a classifier for image classification to generate the skin diagnosis for a skin condition;
wherein the deep neural network determines the skin diagnosis as an integer value on a scale classifying a severity of the skin condition over the image, and the deep neural network further provides an activation map to visualize the skin diagnosis in association with the image; and
wherein the skin diagnostic device is configured to:
perform a plurality (k) of data augmentations to the image to yield k augmented images for processing by the skin analysis unit;
process the k augmented images using the skin analysis unit to obtain k activation maps; and
define a final activation map for the image from the k activation maps to visualize the skin analysis.

2. The diagnostic device of claim 1, wherein the processing unit and storage unit further configure the skin diagnostic device to provide a visualization unit to annotate the image to visualize the skin diagnosis using the final activation map.

3. The diagnostic device of claim 1, wherein the processing unit and storage unit further configure the skin diagnostic device to provide a recommendation unit, responsive to the skin diagnosis, to recommend a product for the skin condition.

4. The diagnostic device of claim 1, wherein the processing unit and storage unit further configure the skin diagnostic device to provide an e-commerce interface with which to purchase products for the skin condition.

5. The diagnostic device of claim 1, wherein the skin condition comprises acne vulgaris and the scale classifying the severity of the skin condition over the image is a global acne severity scale ("GEA").

6. The diagnostic device of claim 1, wherein the deep neural network is configured to receive a normalized face image (x) as input and to output a vector $y=f\theta(x)$ which represents a probability distribution over all possible integer values on the scale and applies an activation function to determine the integer value of the skin diagnosis as a softmax expected value as follows:

$$E[f_\theta(x)]=\Sigma_{i=a}^{b}(f_\theta(x)_i * i)$$

where a, b are the lower and upper bound for the scale.

7. The diagnostic device of claim 1, wherein:
the deep neural network comprises a shared encoder component for the regressor and classifier;
the deep neural network is further configured with one or both of an auxiliary ethnicity prediction component to predict ethnicity and an auxiliary gender prediction component to predict gender; and
the one or both of the auxiliary ethnicity prediction component and the auxiliary gender prediction component share the shared encoder component of the deep neural network.

8. The diagnostic device of claim 1, wherein the deep neural network comprises a convolutional neural network (CNN) for image processing.

9. The diagnostic device of claim 8, wherein the CNN comprises a residual network as an encoder having a global pooling operation before final fully connected layers configured to generate regressor and classifier outputs.

10. The diagnostic device of claim 1, wherein the deep neural network is trained with a combined loss function combining a regressor loss function and a classifier loss function.

11. The diagnostic device of claim 10, wherein the combined loss function conforms to an equation:

$$L = \lambda_{mse} \mathcal{L}_{mse} + \lambda_{ce} \mathcal{L}_{ce} + \lambda_{gender} \mathcal{L}_{gender} + \lambda_{ethnicity} \mathcal{L}_{ethnicity} \quad (2)$$

where:

$\mathcal{L}_{mse}$, $\mathcal{L}_{ce}$, $\mathcal{L}_{gender}$ and $\mathcal{L}_{ethnicity}$ are respective mean square error (MSE), cross-entropy error (CE), gender prediction and ethnicity prediction functions; and $\lambda_{mse}$, $\lambda_{ce}$, $\lambda_{gender}$, and $\lambda_{ethnicity}$ are weighting factors.

12. The diagnostic device of claim 1, wherein each of the k data augmentations comprises one augmentation randomly selected from an affine transformation or a horizontal flip operation.

13. The diagnostic device of claim 1, wherein the deep neural network is configured to apply a Class Activation Mapping (CAM) technique to generate the activation maps.

14. The diagnostic device of claim 1, wherein the diagnostic device comprises one of a smartphone, tablet, laptop, personal computer, or other computing device having or coupled to a camera.

15. The diagnostic device of claim 3, wherein the recommendation unit provides a treatment product selector responsive to the skin diagnosis to obtain at least one of a product recommendation and a treatment plan recommendation.

16. The diagnostic device of claim 1, wherein the skin condition is acne vulgaris.

17. A computer implemented method of skin diagnosis comprising:

receiving an image, that is a selfie face image from a user mobile device;

performing a plurality (k) of data augmentations to the image to yield k augmented images for processing;

processing each of the k augmented images using a deep neural network to obtain k activation maps for a skin diagnosis, the deep neural network further configured to classify image pixels to determine the skin diagnosis for a skin condition, wherein the deep neural network, which is already trained using a dataset of facial image data comprising selfie face images from user mobile devices, is configured as a regressor and a classifier to determine the skin diagnosis as an integer value on a scale classifying a severity of the skin condition over the image, and is configured to provide an activation map to visualize the skin diagnosis;

defining a final activation map for the image from the k activation maps to visualize the skin diagnosis; and visualizing the skin diagnosis in association with the image.

18. The method of claim 17, wherein the deep neural network is further configured with auxiliary tasks to determine one or both of an ethnicity prediction and gender prediction.

19. The method of claim 17, wherein the skin condition comprises acne vulgaris and the scale classifying the severity of the skin condition over the image is a global acne severity scale ("GEA").

20. A computer program product comprising a non-transitory storage device storing instruction that, when executed by a processor of a skin diagnostic device, cause the skin diagnostic device to:

receive an image, that is a selfie face image from a user mobile device;

perform a plurality (k) of data augmentations to the image to yield k augmented images for processing;

process each of the k augmented images using a deep neural network to obtain k activation maps for a skin diagnosis; and define a final activation map for the image from the k activation maps to visualize the skin diagnosis; and wherein the deep neural network is already trained using a dataset of facial image data comprising selfie face images from user mobile devices, and is configured:

to classify image pixels to determine the skin diagnosis for a skin condition, to provide an activation map to visualize the skin diagnosis, as a regressor and a classifier to determine the skin diagnosis, and with auxiliary tasks to determine one or both of an ethnicity prediction and gender prediction.

21. The diagnostic device of claim 1, wherein the final activation map is defined from the k activation maps using one or both of averaging and a threshold applied to eliminate values from the k activation maps.

22. The diagnostic device of claim 1, wherein $2 <= k <= 20$.

* * * * *